US012797534B2

(12) United States Patent
Komai et al.

(10) Patent No.: US 12,797,534 B2
(45) Date of Patent: Nov. 17, 2026

(54) BLOOD COLLECTION CONTAINER, METHOD FOR SEPARATING PLASMA, METHOD FOR SEPARATING EXTRACELLULAR FREE NUCLEIC ACID, AND METHOD FOR SEPARATING EXTRACELLULAR VESICLE

(71) Applicant: SEKISUI MEDICAL CO., LTD., Tokyo (JP)

(72) Inventors: Kuniya Komai, Yamaguchi (JP); Takaya Uchiyama, Yamaguchi (JP); Marika Kanda, Yamaguchi (JP); Tomonori Inoue, Yamaguchi (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 294 days.

(21) Appl. No.: 18/564,326

(22) PCT Filed: May 27, 2022

(86) PCT No.: PCT/JP2022/021743
§ 371 (c)(1),
(2) Date: Nov. 27, 2023

(87) PCT Pub. No.: WO2022/250142
PCT Pub. Date: Dec. 1, 2022

(65) Prior Publication Data

US 2024/0245844 A1 Jul. 25, 2024

(30) Foreign Application Priority Data

May 28, 2021 (JP) ................................. 2021-090433

(51) Int. Cl.
*A61M 1/36* (2006.01)
*A61J 1/05* (2006.01)

(52) U.S. Cl.
CPC .............. *A61M 1/3693* (2013.01); *A61J 1/05* (2013.01)

(58) Field of Classification Search
CPC .. B01L 3/50215; B01L 3/5021; B01L 3/5082; B01L 3/50; B01L 2200/0631;
(Continued)

(56) References Cited

U.S. PATENT DOCUMENTS 3,852,194 A * 12/1974 Zine, Jr. ............... G01N 33/491 494/81
2002/0169408 A1* 11/2002 Beretta .................. B01D 33/15 604/19

(Continued)

FOREIGN PATENT DOCUMENTS

CN 102209895 10/2011
CN 107209169 9/2017

(Continued)

OTHER PUBLICATIONS

Percentage Concentration to Molarity Calculator. https://www.omnicalculator.com/chemistry/percentage-concentration-to-molarity. Accessed Dec. 15, 2025 Mon.*

(Continued)

*Primary Examiner* — Adam Marcetich
(74) *Attorney, Agent, or Firm* — Wenderoth, Lind & Ponack, L.L.P.

(57) ABSTRACT

Provided is a blood collection container capable of suppressing contamination of plasma by white blood cells and components in white blood cells. A blood collection container according to the present invention includes a blood collection container main body, a plasma separation material stored in the blood collection container main body, and an aqueous solution stored in the blood collection container main body, in which a solute contained in the aqueous
(Continued)

solution contains an anticoagulant, and a total concentration of the solute in the aqueous solution is 100 mM or more and 450 mM or less, or 1200 mM or more.

23 Claims, 1 Drawing Sheet

(58) Field of Classification Search
CPC .. G01N 33/491; G01N 21/07; A61B 5/15003; A61B 5/154; A61B 5/150755; A61B 10/0045; A61J 1/2013; A61J 1/201; A61J 1/05; A61M 1/3693; A61M 1/029; A61M 2202/0415; A61M 2202/0427; A61M 1/3672
See application file for complete search history.

(56) References Cited

U.S. PATENT DOCUMENTS

| | | | | |
|---|---|---|---|---|
| 2003/0073650 | A1* | 4/2003 | Reddy | A61K 41/17 435/2 |
| 2003/0215784 | A1* | 11/2003 | Dumont | A61K 41/17 435/2 |
| 2004/0043505 | A1* | 3/2004 | Walenciak | A61B 5/150755 422/400 |
| 2005/0170327 | A1* | 8/2005 | Sumida | A61K 35/16 435/2 |
| 2011/0250105 | A1 | 10/2011 | Suto et al. | |
| 2013/0183655 | A1* | 7/2013 | Monroe | A61B 5/15003 435/283.1 |
| 2014/0360944 | A1* | 12/2014 | Esteron | B01D 21/262 210/698 |
| 2016/0045658 | A1* | 2/2016 | Åhl | A61K 31/7004 424/602 |
| 2018/0092806 | A1 | 4/2018 | Okamoto et al. | |
| 2018/0110917 | A1* | 4/2018 | Turzi | A61P 17/00 |
| 2018/0136192 | A1* | 5/2018 | Anraku | G01N 33/491 |
| 2018/0168142 | A1* | 6/2018 | Wegener | A61K 35/14 |
| 2018/0296748 | A1* | 10/2018 | Emerson | A61J 1/2072 |
| 2019/0254273 | A1* | 8/2019 | Fernando | G01N 33/6893 |
| 2019/0313958 | A1* | 10/2019 | Urano | A61B 5/150351 |
| 2020/0196594 | A1 | 6/2020 | Birnboim et al. | |
| 2020/0300838 | A1* | 9/2020 | Desharnais | A01N 1/122 |
| 2021/0132036 | A1* | 5/2021 | Carlson | G01N 1/10 |
| 2021/0146030 | A1* | 5/2021 | Josephs | A61M 1/3679 |
| 2021/0371848 | A1 | 12/2021 | George et al. | |
| 2022/0088589 | A1* | 3/2022 | Batra | B01D 17/0217 |

FOREIGN PATENT DOCUMENTS

| | | |
|---|---|---|
| CN | 109266531 | 1/2019 |
| CN | 111372451 | 7/2020 |
| JP | 2001-83144 | 3/2001 |
| JP | 2005-17189 | 1/2005 |
| JP | 2021-500585 | 1/2021 |
| WO | 2010/053180 | 5/2010 |
| WO | 2010/132783 | 11/2010 |
| WO | 2016/159236 | 10/2016 |
| WO | 2020/132747 | 7/2020 |

OTHER PUBLICATIONS

Extended European Search Report issued May 8, 2025 in European Patent Application No. 22811410.4.

International Preliminary Report on Patentability issued Nov. 21, 2023 in International (PCT) Application No. PCT/JP2022/021743.

International Search Report issued Aug. 9, 2022 in International (PCT) Application No. PCT/JP2022/021743.

* cited by examiner

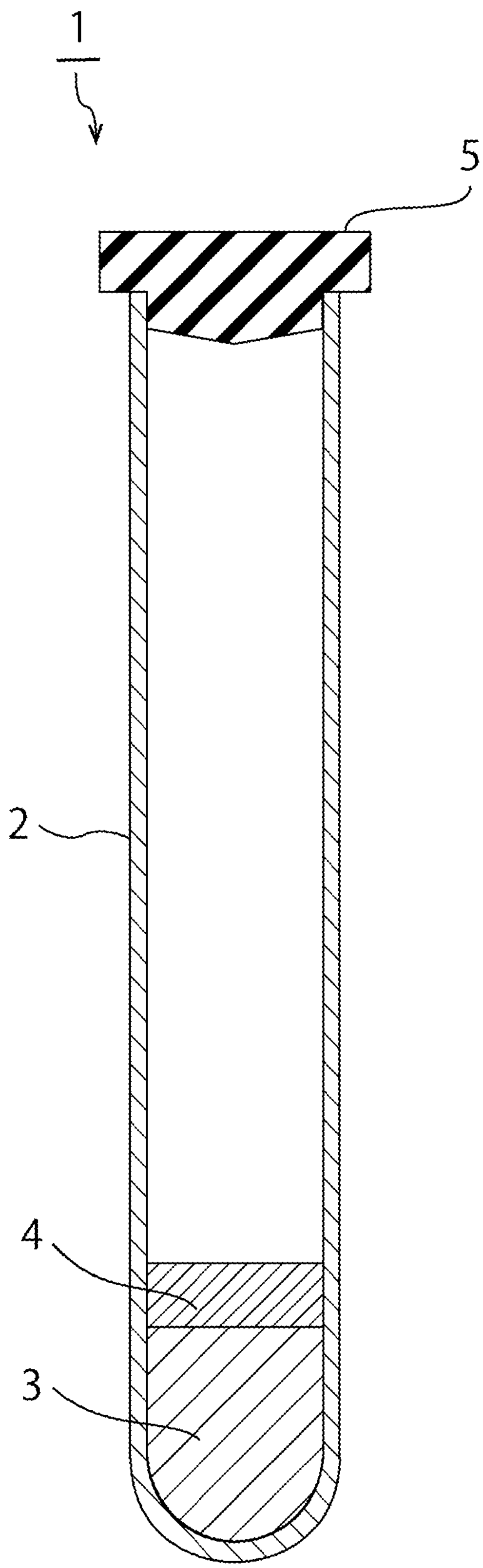
1
5
2
4
3

BLOOD COLLECTION CONTAINER, METHOD FOR SEPARATING PLASMA, METHOD FOR SEPARATING EXTRACELLULAR FREE NUCLEIC ACID, AND METHOD FOR SEPARATING EXTRACELLULAR VESICLE

TECHNICAL FIELD

The present invention relates to a blood collection container. Further, the present invention relates to a method for separating plasma, a method for separating cell free nucleic acids, and a method for separating extracellular vesicles using the blood collection container.

BACKGROUND ART

In clinical laboratory tests, a blood collection container such as a blood collection tube is widely used to collect blood. After blood is collected in the blood collection container storing a plasma separation material, the blood can be separated into plasma and blood cells by centrifuging the blood collection container. At this time, the plasma is located above the plasma separation material, and the blood cells are located below the plasma separation material. As a blood collection container storing a plasma separation material, a blood collection container (for example, Patent Document 1) storing a composition for plasma separation that includes a resin, an inorganic powder, and the like, and a blood collection container (for example, Patent Document 2) storing a jig for plasma separation are known.

Further, Patent Document 3 below describes a device for separating extracellular DNA in blood.

RELATED ART DOCUMENT

Patent Document

Patent Document 1: WO 2010/053180 A1
Patent Document 2: WO 2010/132783 A1
Patent Document 3: WO 2020/132747 A1

SUMMARY OF THE INVENTION

Problems to be Solved by the Invention

In clinical laboratory tests, tests using plasma are carried out. When plasma is separated from blood using a conventional blood collection container as described in Patent Documents 1 and 2, the separated plasma may be contaminated by a relatively large amount of white blood cells. When the plasma is contaminated by a relatively large amount of white blood cells, the white blood cells may be destroyed over time during storage of a specimen, and components such as proteins and nucleic acids in the white blood cells may leak into the plasma, affecting test results.

For example, in a test for detecting cell free nucleic acids (for example, cell free DNA) in plasma, the test results greatly vary depending on nucleic acids leaking from the white blood cells.

In the device described in Patent Document 3, contamination of plasma by white blood cells can be suppressed to some extent, but an effect thereof may not be sufficient. Therefore, even in the device described in Patent Document 3, components such as nucleic acids in the white blood cells may leak into the plasma over time during storage of a specimen, affecting the test results.

An object of the present invention is to provide a blood collection container capable of suppressing contamination of plasma by white blood cells and components in white blood cells. Another object of the present invention is to provide a method for separating plasma, a method for separating cell free nucleic acids, and a method for separating extracellular vesicles using the blood collection container.

Means for Solving the Problems

According to a broad aspect of the present invention, there is provided a blood collection container including a blood collection container main body, a plasma separation material stored in the blood collection container main body, and an aqueous solution stored in the blood collection container main body, a solute contained in the aqueous solution containing an anticoagulant, and the solute in the aqueous solution having a total concentration of 100 mM or more and 450 mM or less, or 1200 mM or more.

In a specific aspect of the blood collection container according to the present invention, the total concentration of the solute in the aqueous solution is 250 mM or more and 390 mM or less, or 1200 mM or more and 6500 mM or less.

In a specific aspect of the blood collection container according to the present invention, the solute contained in the aqueous solution contains a second solute other than an anticoagulant, and the second solute includes an inorganic salt or a saccharide.

In a specific aspect of the blood collection container according to the present invention, the second solute includes an inorganic salt, and the inorganic salt includes a sodium salt or a potassium salt.

In a specific aspect of the blood collection container according to the present invention, the second solute includes a saccharide, and the saccharide includes glucose, sucrose, or trehalose.

In a specific aspect of the blood collection container according to the present invention, the anticoagulant is EDTA, a metal salt of EDTA, heparin, a metal salt of heparin, or sodium citrate.

In a specific aspect of the blood collection container according to the present invention, the blood collection container is a blood collection container in which a predetermined amount of blood is collected, and when physiological saline in an amount equivalent to a predetermined amount of blood collected in the blood collection container is collected in the blood collection container to obtain a mixed liquid in which the physiological saline and the aqueous solution are mixed, an osmotic pressure of the mixed liquid is 330 mOsm/L or more and 380 mOsm/L or less, or 440 mOsm/L or more and 1300 mOsm/L or less.

In a specific aspect of the blood collection container according to the present invention, a specific gravity of the plasma separation material at 25° C. is 1.030 or more and 1.120 or less.

In a specific aspect of the blood collection container according to the present invention, the plasma separation material is a composition for plasma separation.

In a specific aspect of the blood collection container according to the present invention, the composition for plasma separation contains an organic component having fluidity at 25° C. and an inorganic fine powder, the organic component includes a resin, and the inorganic fine powder includes fine powder silica.

In a specific aspect of the blood collection container according to the present invention, the fine powder silica includes hydrophilic silica.

In a specific aspect of the blood collection container according to the present invention, a content of the hydrophilic silica is 0.01 wt % or more and 2.50 wt % or less in 100 wt % of the composition for plasma separation.

In a specific aspect of the blood collection container according to the present invention, the fine powder silica includes hydrophilic silica and hydrophobic silica.

In a specific aspect of the blood collection container according to the present invention, the specific gravity of the composition for plasma separation at 25° C. is 1.050 or more, and the inorganic fine powder contains an inorganic fine powder having a specific gravity larger than the specific gravity of the fine powder silica.

In a specific aspect of the blood collection container according to the present invention, the resin includes a petroleum resin, a cyclopentadiene-based resin, a polyester resin, or a (meth)acrylic resin.

In a specific aspect of the blood collection container according to the present invention, the blood collection container is used to separate cell free nucleic acids or extracellular vesicles in blood.

According to a broad aspect of the present invention, there is provided a method for separating plasma, the method including a step of collecting blood in the blood collection container described above and a step of centrifuging the blood collection container in which the blood has been collected.

According to a broad aspect of the present invention, there is provided a method for separating cell free nucleic acids, the method including: a step of collecting blood in the blood collection container described above; a step of centrifuging the blood collection container in which the blood has been collected to separate plasma from the blood; and a step of separating cell free nucleic acids from the separated plasma.

According to a broad aspect of the present invention, there is provided a method for separating extracellular vesicles, the method including: a step of collecting blood in the blood collection container described above; a step of centrifuging the blood collection container in which the blood has been collected to separate plasma from the blood; and a step of separating extracellular vesicles from the separated plasma.

Effect of the Invention

A blood collection container according to the present invention includes a blood collection container main body, a plasma separation material stored in the blood collection container main body, and an aqueous solution stored in the blood collection container main body. In the blood collection container according to the present invention, a solute in the aqueous solution contains an anticoagulant, and the total concentration of the solute in the aqueous solution is 100 mM or more and 450 mM or less, or 1200 mM or more. Since the blood collection container according to the present invention is provided with the configuration described above, it is possible to suppress contamination of plasma by white blood cells and components in white blood cells.

BRIEF DESCRIPTION OF DRAWINGS

FIG. 1 is a front cross-sectional view schematically illustrating a blood collection container according to one embodiment of the present invention.

MODE (S) FOR CARRYING OUT THE INVENTION

Hereinafter, the present invention will be described in detail.

A blood collection container according to the present invention includes a blood collection container main body, a plasma separation material stored in the blood collection container main body, and an aqueous solution stored in the blood collection container main body. In the blood collection container according to the present invention, a solute contained in the aqueous solution contains an anticoagulant, and the total concentration of the solute in the aqueous solution is 100 mM or more and 450 mM or less, or 1200 mM or more.

Since the blood collection container according to the present invention is provided with the configuration described above, it is possible to suppress contamination of plasma by white blood cells and components in white blood cells.

Further, since the blood collection container according to the present invention is provided with the configuration described above, contamination of plasma by red blood cells can also be suppressed.

When plasma is separated from blood using a conventional blood collection container, the separated plasma may be contaminated by a relatively large amount of white blood cells. When the plasma is contaminated by a relatively large amount of white blood cells, components in the white blood cells may leak into the plasma, affecting a test using plasma. In a conventional blood collection container, it is difficult to sufficiently suppress contamination of plasma by white blood cells and components in white blood cells. Note that, in order to suppress an influence on test results, a blood collection container storing a cell stabilizing agent that stabilizes blood cells may be used, but the cell stabilizing agent is expensive, and may cause harm to a human body and the environment depending on a type and concentration.

On the other hand, in the blood collection container according to the present invention, it is possible to effectively suppress contamination of plasma by white blood cells and components in white blood cells. When blood is collected in the blood collection container according to the present invention, the blood and the aqueous solution are mixed, and the osmotic pressure of the blood increases. Therefore, water in the white blood cells and water in the red blood cells move to the outside of the blood cells, and the specific gravity of the white blood cells and the red blood cells increases. The white blood cells and the red blood cells with increased specific gravity move downward better than the plasma separation material having a certain specific gravity by centrifuging the blood collection container. As a result, contamination of plasma by white blood cells and red blood cells can be suppressed. Note that, when the osmotic pressure of the blood after collection is not appropriate, stress is applied to blood cells, and white blood cells by which the plasma is contaminated are damaged even after centrifugation, and components in the white blood cells easily leak into the plasma. On the other hand, in the blood collection container according to the present invention, since the concentration of the solute is in an appropriate range, the stress on the blood cells is suppressed, and leakage of contents from the blood cells by which the plasma is contaminated can also be effectively suppressed.

Hereinafter, details and the like of the blood collection container according to the present invention will be described. Note that, in the present specification, the term "(meth)acryl" means one or both of "acryl" and "methacryl".

(Plasma Separation Material)

The blood collection container includes a plasma separation material stored in the blood collection container main body. As the plasma separation material, a conventionally known plasma separation material can be used. Examples of the plasma separation material include a composition for plasma separation and a jig for plasma separation. The plasma separation material is preferably the composition for plasma separation because it is easy to prepare a plasma separation material.

The specific gravity of the plasma separation material at 25° C. may be 1.030 or more, 1.040 or more, 1.050 or more, 1.060 or more, more than 1.060, or 1.070 or more. The specific gravity of the plasma separation material at 25° C. may be 1.120 or less, 1.100 or less, 1.080 or less, less than 1.070, less than 1.060, less than 1.050, or less than 1.040.

A storage location of the plasma separation material is not particularly limited as long as it is in the blood collection container main body. The plasma separation material may be disposed on a bottom portion of the blood collection container main body, may be disposed on an inner wall surface of the blood collection container main body, or may be disposed on a side wall surface of the blood collection container main body.

<Composition for Plasma Separation>

The composition for plasma separation is a composition that moves between a plasma layer and a blood cell layer during centrifugation to form a septal wall. Further, the composition for plasma separation is used for a purpose of preventing component migration between the plasma layer and the blood cell layer after centrifugation. The composition for plasma separation preferably has thixotropic properties. The composition for plasma separation may be stored in the bottom portion of the blood collection container main body or may be disposed on the side wall surface of the blood collection container main body. From a viewpoint of more effectively exhibiting the effect of the present invention, it is preferable that the composition for plasma separation is stored in the bottom portion of the blood collection container main body.

As the composition for plasma separation, a conventionally known composition for plasma separation can be used.

The composition for plasma separation preferably contains an organic component having fluidity at 25° C. and an inorganic fine powder. Only one kind of each of the organic component having fluidity at 25° ° C. and the inorganic fine powder may be used, and two or more kinds thereof may be used in combination.

Organic component having fluidity at 25° C.:

The phrase "having fluidity at 25° C." means that viscosity at 25° ° C. is 500 Pa·s or less.

The viscosity of the organic component at 25° C. is preferably 30 Pa·s or more, and more preferably 50 Pa·s or more, meanwhile preferably 200 Pa·s or less, and more preferably 100 Pa·s or less. When the viscosity is the above lower limit or more and the above upper limit or less, the fluidity of the composition for plasma separation is enhanced, and strength of the septal wall can be enhanced.

The viscosity of the organic component at 25° C. is measured using an E-type viscometer (for example, "TVE-35" manufactured by Toki Sangyo Co., Ltd.) under conditions of 25° C. and a shear rate of 1.0 second$^{-1}$.

Examples of the organic component include a resin and a mixture of a resin and an organic compound such as a plasticizer. Therefore, the organic component preferably contains the resin, and more preferably contains the resin and the organic compound. When the organic component is a mixture of the resin and the organic compound, the resin or the organic compound may not have fluidity as long as the mixture (the organic component) has fluidity. When the organic component is a mixture of the resin and the organic compound, the resin may be, for example, a resin that is solid at 25° C. Only one kind of each of the resin and the organic compound may be used, or two or more kinds thereof may be used in combination.

Examples of the resin include a petroleum resin, a cyclopentadiene-based resin, a polyester resin, a polyurethane resin, a (meth)acrylic resin, a silicone resin, an α-olefin-fumaric acid ester copolymer, a copolymer of sebacic acid, 2,2-dimethyl-1,3-propanediol, and 1,2-propanediol, a polyether polyurethane resin, and a polyether polyester resin. Only one kind of the resin may be used, and two or more kinds thereof may be used in combination.

The resin preferably includes a petroleum resin, a cyclopentadiene-based resin, a polyester resin, or a (meth)acrylic resin.

Examples of commercially available products of the petroleum resin include "REGALITE S5090" manufactured by Eastman Chemical Company.

Examples of the cyclopentadiene-based resin include a polymer of a cyclopentadiene monomer, a copolymer of a cyclopentadiene monomer and an aromatic monomer, and a dicyclopentadiene resin. The cyclopentadiene-based resin may be hydrogenated. The polymer of the cyclopentadiene monomer and the copolymer of the cyclopentadiene monomer and the aromatic monomer may be oligomers.

Examples of the cyclopentadiene monomer include cyclopentadiene, dicyclopentadiene, and alkyl-substituted derivatives of cyclopentadiene.

Examples of the aromatic monomer include styrene, methyl styrene, indene, and methylindene.

Examples of commercially available products of the dicyclopentadiene resin include "SUKOREZ SU500" and "SUKOREZ SU90" manufactured by Kolon Industries Inc.

Examples of the polyester resin include a polyalkylene terephthalate resin and a polyalkylene naphthalate resin. Examples of the polyalkylene terephthalate resin include polyethylene terephthalate, polybutylene terephthalate, and poly-1,4-cyclohexane dimethylene terephthalate.

Examples of the polyurethane resin include a reactant of a polyol compound and an isocyanate compound.

Examples of the (meth)acrylic resin include a resin obtained by polymerizing at least one (meth)acrylic acid ester monomer, and a resin obtained by polymerizing at least one (meth)acrylic acid ester monomer and at least one monomer other than the (meth)acrylic acid ester monomer.

Examples of the (meth)acrylic acid ester monomer include (meth)acrylic acid alkyl ester, (meth)acrylic acid polyalkylene glycol ester, (meth)acrylic acid alkoxy alkyl ester, (meth)acrylic acid hydroxyalkyl ester, (meth)acrylic acid glycidyl ester, (meth)acrylic acid dialkylamino alkyl ester, (meth)acrylic acid benzyl ester, (meth)acrylic acid phenoxy alkyl ester, (meth)acrylic acid cyclohexyl ester, (meth)acrylic acid isobornyl ester, and (meth)acrylic acid alkoxysilyl alkyl ester, having an alkyl group having 1 to carbon atoms. Only one kind of the (meth)acrylic acid ester monomer may be used, or two or more kinds thereof may be used in combination.

Examples of the organic compound include benzene polycarboxylic acid alkyl ester derivatives. The organic compound is preferably a benzene polycarboxylic acid alkyl ester derivative. Therefore, the organic component is preferably a mixture of the resin and the benzene polycarboxylic acid alkyl ester derivative.

Examples of the benzene polycarboxylic acid alkyl ester derivative include a phthalic acid ester, a trimellitic acid ester, and a pyromellitic acid ester. Only one kind of the benzene polycarboxylic acid alkyl ester derivative may be used, or two or more kinds thereof may be used in combination.

Examples of the trimellitic acid ester include trin-octyl trimellitate, tri-iso-octyl trimellitate, and tri-isodecyl trimellitate.

Examples of the pyromellitic acid ester include tetraisooctyl pyromellitic acid.

Examples of commercially available products of the trimellitic acid ester include "MONOCIZER W700" and "MONOCIZER W-750" manufactured by DIC Corporation, and "SANSO CIZER TOTM" and "SANSO CIZER TITM" manufactured by New Japan Chemical Co., Ltd.

Examples of commercially available products of the pyromellitic acid ester include "MONOCIZER W-7010" manufactured by DIC Corporation.

The benzene polycarboxylic acid alkyl ester derivative is preferably a phthalic acid ester, a trimellitic acid ester, or a pyromellitic acid ester, and more preferably a trimellitic acid ester.

The content of the organic component in 100 wt % of the composition for plasma separation is preferably 80 wt % or more, more preferably 85 wt % or more, and still more preferably 90 wt % or more, meanwhile preferably 97 wt % or less.

Inorganic Fine Powder:

Examples of the inorganic fine powder include fine powder silica, titanium oxide powder, calcium carbonate powder, zinc oxide powder, alumina powder, glass powder, talc powder, kaolin powder, bentonite powder, titania powder, and zirconium powder.

From the viewpoint of more effectively exhibiting the effect of the present invention, the inorganic fine powder preferably contains fine powder silica. When a composition for plasma separation having a specific gravity at 25° ° C. of 1.050 or more is obtained, the inorganic fine powder more preferably contains fine powder silica and an inorganic fine powder (a second inorganic fine powder) other than the fine powder silica. However, even when the specific gravity of the composition for plasma separation at 25° C. is 1.050 or more, the inorganic fine powder may not contain the second inorganic fine powder. Further, even when the specific gravity of the composition for plasma separation at 25° ° C. is less than 1.050, the inorganic fine powder may contain the second inorganic fine powder. Only one kind of each of the inorganic fine powder, the fine powder silica, and the second inorganic fine powder may be used, or two or more kinds thereof may be used in combination.

Examples of the fine powder silica include natural silica and synthetic silica. Examples of the synthetic silica include hydrophilic silica and hydrophobic silica. Hydrophilic silica has an action of imparting thixotropic properties to the composition for plasma separation and adjusting the specific gravity, for example, by hydrogen bonding between hydroxyl groups on a particle surface. On the other hand, hydrophobic silica has a smaller thixotropic imparting effect than hydrophilic silica.

From a viewpoint of maintaining both the specific gravity and the thixotropic properties of the composition for plasma separation in a suitable range, the fine powder silica preferably contains hydrophilic silica, and more preferably contains hydrophilic silica and hydrophobic silica. The fine powder silica preferably contains at least hydrophilic silica.

The second inorganic fine powder is preferably an inorganic fine powder having a specific gravity larger than the specific gravity of fine powder silica, and more preferably an inorganic fine powder having a specific gravity of 3 or more, such as zinc oxide powder, titanium oxide powder, or alumina powder.

The specific gravity of the second inorganic fine powder is preferably 3 or more, more preferably 3.5 or more, and still more preferably 4 or more. The specific gravity of the second inorganic fine powder is preferably as large as possible. When the specific gravity is the above lower limit or more, the specific gravity of the composition for plasma separation can be effectively increased.

An average particle diameter of the inorganic fine powder, the fine powder silica, and the second inorganic fine powder is not particularly limited. The average particle diameter of the inorganic fine powder, the fine powder silica, and the second inorganic fine powder may be 1 nm or more, 10 nm or more, 500 nm or less, or 100 nm or less.

The average particle diameter of the inorganic fine powder, the fine powder silica, and the second inorganic fine powder is an average diameter measured on a volume basis, and is a value of a median diameter (D50) of 50%. The volume average particle diameter (D50) can be measured by a laser diffraction/scattering method, an image analysis method, a Coulter method, a centrifugal sedimentation method, or the like. The volume average particle diameter (D50) is preferably determined by measurement by a laser diffraction/scattering method or an image analysis method.

A specific surface area of the fine powder silica is not particularly limited. The specific surface area of the fine powder silica may be 20 $m^2/g$ or more, 100 $m^2/g$ or more, 500 $m^2/g$ or less, or 300 $m^2/g$ or less.

The specific surface area of the fine powder silica is measured by a BET method.

The content of the hydrophilic silica in 100 wt % of the composition for plasma separation is preferably 0.01 wt % or more, more preferably 0.10 wt % or more, and still more preferably 0.30 wt % or more, meanwhile preferably 2.50 wt % or less, and more preferably 2.00 wt % or less. When the content of the hydrophilic silica is the above lower limit or more and the above upper limit or less, both the specific gravity and thixotropy properties of the composition for plasma separation can be maintained in a more suitable range.

The content of the fine powder silica in 100 wt % of the composition for plasma separation is preferably 0.1 wt % or more, and more preferably 0.5 wt % or more, meanwhile preferably 10 wt % or less, and more preferably 7 wt % or less. When the content of the fine powder silica is the above lower limit or more and the above upper limit or less, both the specific gravity and thixotropy properties of the composition for plasma separation can be maintained in a more suitable range.

The content of the second inorganic fine powder in 100 wt % of the composition for plasma separation is preferably 0.01 wt % or more, and more preferably 0.1 wt % or more, meanwhile preferably 10 wt % or less, and more preferably 7 wt % or less. When the content of the second inorganic fine powder is the above lower limit or more and the above upper limit or less, the specific gravity of the composition for plasma separation can be effectively increased.

The content of the inorganic fine powder in 100 wt % of the composition for plasma separation is preferably 0.1 wt % or more, and more preferably 0.5 wt % or more, meanwhile preferably 10 wt % or less, and more preferably 7 wt % or less. When the content of the inorganic fine powder is the above lower limit or more and the above upper limit or less, the specific gravity of the composition for plasma separation can be effectively increased.

Other Components:

The composition for plasma separation may contain components other than the components described above as long as the effect of the present invention is not impaired. Examples of the other components include an organic gelling agent, a thermoplastic elastomer, a polyalkylene glycol, a silicone oil, an auxiliary solvent, an antioxidant, a colorant, and water. Only one kind of each of the other components may be used, and two or more kinds thereof may be used in combination.

The specific gravity of the composition for plasma separation at 25° C. is preferably 1.030 or more, and more preferably 1.040 or more, meanwhile preferably 1.120 or less. When the specific gravity of the composition for plasma separation at 25° C. is the above lower limit or more and the above upper limit or less, the effect of the present invention can be more effectively exhibited.

Note that, the specific gravity of the composition for plasma separation at 25° C. may be 1.050 or more, 1.060 or more, more than 1.060, or 1.070 or more. The specific gravity of the composition for plasma separation at 25° C. may be 1.100 or less, 1.080 or less, less than 1.070, less than 1.060, less than 1.050, or less than 1.040.

One drop of the composition for plasma separation is sequentially added dropwise into a saline solution at 25° C. in which the specific gravity is adjusted stepwise at an interval of 0.002, and the specific gravity of the composition for plasma separation at 25° C. is measured by floating and sinking in the saline solution.

The viscosity of the composition for plasma separation at 25° C. is preferably 100 Pa·s or more, and more preferably 150 Pa·s or more, meanwhile preferably 500 Pa·s or less, and more preferably 400 Pa·s or less. When the viscosity is the above lower limit or more and the above upper limit or less, the effect of the present invention can be more effectively exhibited.

The viscosity of the composition for plasma separation at 25° C. is measured under the conditions of 25° C. and a shear rate of 1.0 $second^{-1}$ using an E-type viscometer (for example, "TVE-35" manufactured by Toki Sangyo Co., Ltd.).

<Jig for Plasma Separation>

The jig for plasma separation is a jig that moves between a plasma layer and a blood cell layer during centrifugation to form a septal wall. Further, the jig for plasma separation is used for the purpose of preventing component migration between the plasma layer and the blood cell layer.

As the jig for plasma separation, a conventionally known jig for plasma separation can be used. Examples of the jig for plasma separation include a mechanical separator (a jig for plasma separation) described in WO 2010/132783 A1 and the like.

Examples of a material of the jig for plasma separation include elastomer.

(Aqueous Solution)

The blood collection container includes an aqueous solution stored in the blood collection container main body. The aqueous solution contains an anticoagulant and water. The solute contained in the aqueous solution contains an anticoagulant. The aqueous solution preferably contains a second solute other than an anticoagulant. Therefore, the aqueous solution preferably contains an anticoagulant (a first solute), a second solute, and water. The solute contained in the aqueous solution preferably contains an anticoagulant (a first solute) and a second solute.

From a viewpoint of exhibiting the effect of the present invention, the total concentration of the solute in the aqueous solution is 100 mM or more and 450 mM or less, or 1200 mM or more. In other words, the total concentration of the solute in the aqueous solution is 100 mmol/L or more and 450 mmol/L or less, or 1200 mmol/L or more. When the aqueous solution contains only an anticoagulant as a solute, the total concentration of the solute is the concentration of the anticoagulant. When the aqueous solution contains an anticoagulant and a second solute as the solute, the total concentration of the solute is the sum of the concentration of the anticoagulant and the concentration of the second solute. The concentration of the anticoagulant is the concentration of the anticoagulant in the aqueous solution when the aqueous solution contains only one kind of anticoagulant, and the concentration of the anticoagulant is the total concentration of the anticoagulant in the aqueous solution when the aqueous solution contains two or more kinds of anticoagulant. The concentration of the second solute is the concentration of the second solute in the aqueous solution when the aqueous solution contains only one kind of second solute, and the concentration of the second is the total concentration of the second solute in the aqueous solution when the aqueous solution contains two or more kinds of second solute. For example, when the aqueous solution contains three types of solutes, that is, an anticoagulant (X), a second solute (Y), and a second solute (Z), and their concentrations (mM) are A, B, and C, respectively, the total concentration of the solutes in the aqueous solution is (A+B+C) mM.

The total concentration of the solute in the aqueous solution is preferably the total concentration of components other than water contained in the aqueous solution.

The total concentration of the solute in the aqueous solution may be 100 mM or more and 450 mM or less, or 1200 mM or more.

When the total concentration of the solutes in the aqueous solution is 100 mM or more and 450 mM or less, the total concentration of the solutes in the aqueous solution is preferably 250 mM or more, and more preferably 300 mM or more, meanwhile preferably 390 mM or less, and more preferably 380 mM or less. When the total concentration of the solutes is the above lower limit or more and the above upper limit or less, the effect of the present invention can be more effectively exhibited.

When the total concentration of the solutes in the aqueous solution is 1200 mM or more, the total concentration of the solutes in the aqueous solution is preferably 1500 mM or more, and more preferably 2000 mM or more, meanwhile preferably 7000 mM or less, and more preferably 6500 mM or less. When the total concentration of the solutes is the above lower limit or more and the above upper limit or less, the effect of the present invention can be more effectively exhibited.

<Anticoagulant (First Solute)>

The aqueous solution contains an anticoagulant. As the anticoagulant, a conventionally known anticoagulant can be used. Only one kind of the anticoagulant may be used, or two or more kinds thereof may be used in combination.

Examples of the anticoagulant include heparin, a metal salt of heparin, ethylenediaminetetraacetic acid (EDTA), a metal salt of EDTA, and citric acid.

From a viewpoint of favorably exhibiting anticoagulation performance, the anticoagulant is preferably EDTA, a metal salt of EDTA, heparin, a metal salt of heparin, or sodium citrate.

The concentration of the anticoagulant in the aqueous solution is preferably 2 mM or more, more preferably 5 mM or more, and still more preferably 10 mM or more, meanwhile preferably 2000 mM or less, more preferably 1000 mM or less, still more preferably 500 mM or less, still more preferably 250 mM or less, still more preferably 100 mM or less, and particularly preferably 50 mM or less. When the concentration of the anticoagulant is the above lower limit or more and the above upper limit or less, the anticoagulation performance can be favorably exhibited.

<Second Solute>

The second solute is a solute other than the anticoagulant contained in the aqueous solution. By using the second solute, the osmotic pressure of the blood collected in the blood collection container can be effectively increased without excessively increasing the content of the anticoagulant. Only one kind of the second solute may be used, or two or more kinds thereof may be used in combination.

The second solute is not particularly limited as long as it is a component other than the anticoagulant. Examples of the second solute include inorganic salts, saccharides, sugar alcohols, propylene glycol, and polyethylene glycol (PEG).

Examples of the inorganic salt include sodium salts such as sodium chloride and sodium hydrogen phosphate, and potassium salts such as potassium chloride and potassium hydrogen carbonate.

Examples of the saccharide include monosaccharides, disaccharides, and polysaccharides. Examples of the monosaccharide include glucose, dihydroxyacetone, fructose, and galactose. Examples of the disaccharide include sucrose, trehalose, maltose, and lactulose. Examples of the polysaccharide include dextran, hydroxyethyl starch, methyl cellulose, and poly sucrose.

Examples of the sugar alcohol include D-mannitol and D-sorbitol.

The second solute preferably contains an inorganic salt or a saccharide. In this case, the effect of the present invention can be more effectively exhibited.

The inorganic salt preferably contains a sodium salt or a potassium salt, and more preferably contains sodium chloride or potassium chloride. In this case, the effect of the present invention can be more effectively exhibited.

The saccharide preferably contains glucose, sucrose, or trehalose. In this case, the effect of the present invention can be more effectively exhibited.

When the total concentration of the solute in the aqueous solution is 100 mM or more and 450 mM or less, the concentration of the inorganic salt in the aqueous solution is preferably 100 mM or more, more preferably 200 mM or more, and still more preferably 300 mM or more, meanwhile preferably 450 mM or less, more preferably 420 mM or less, and still more preferably 400 mM or less. When the concentration of the inorganic salt is the above lower limit or more and the above upper limit or less, the effect of the present invention can be further more effectively exhibited.

When the total concentration of the solute in the aqueous solution is 1200 mM or more, the concentration of the inorganic salt in the aqueous solution is preferably 400 mM or more, more preferably 500 mM or more, and still more preferably 1000 mM or more, meanwhile preferably 5000 mM or less, more preferably 2000 mM or less, and still more preferably 1500 mM or less. When the concentration of the inorganic salt is the above lower limit or more and the above upper limit or less, the effect of the present invention can be further more effectively exhibited.

When the aqueous solution contains only one kind of inorganic salt, the concentration of the inorganic salt is the concentration of the inorganic salt in the aqueous solution, and when the aqueous solution contains two or more kinds of inorganic salt, the concentration of the inorganic salt is the total concentrations of the inorganic salts in the aqueous solution.

When the total concentration of the solute in the aqueous solution is 100 mM or more and 450 mM or less, the concentration of the saccharide in the aqueous solution is preferably 100 mM or more, more preferably 200 mM or more, and still more preferably 300 mM or more, meanwhile preferably 450 mM or less, more preferably 420 mM or less, and still more preferably 400 mM or less. When the concentration of the saccharide is the above lower limit or more and the above upper limit or less, the effect of the present invention can be further more effectively exhibited.

When the total concentration of the solute in the aqueous solution is 1200 mM or more, the concentration of the saccharide in the aqueous solution is preferably 400 mM or more, more preferably 500 mM or more, and still more preferably 1000 mM or more, meanwhile preferably 5000 mM or less, more preferably 3000 mM or less, and still more preferably 2500 mM or less. When the concentration of the saccharide is the above lower limit or more and the above upper limit or less, the effect of the present invention can be further more effectively exhibited.

When the aqueous solution contains only one kind of saccharide, the concentration of the saccharide is the concentration of the saccharide in the aqueous solution, and when the aqueous solution contains two or more kinds of saccharides, the concentration of the saccharide is the total concentration of the saccharides in the aqueous solution.

When the total concentration of the solute in the aqueous solution is 100 mM or more and 450 mM or less, the concentration of the second solute in the aqueous solution is preferably 80 mM or more, more preferably 100 mM or more, and still more preferably 300 mM or more, meanwhile preferably 450 mM or less, more preferably 420 mM or less, and still more preferably 400 mM or less. When the concentration of the second solute is the above lower limit or more and the above upper limit or less, the effect of the present invention can be further more effectively exhibited.

When the total concentration of the solute in the aqueous solution is 1200 mM or more, the concentration of the second solute in the aqueous solution is preferably 400 mM or more, more preferably 1000 mM or more, and still more preferably 2000 mM or more, meanwhile preferably 7000 mM or less, more preferably 6500 mM or less, and still more preferably 6000 mM or less. When the concentration of the second solute is the above lower limit or more and the above upper limit or less, the effect of the present invention can be further more effectively exhibited.

The amount of the aqueous solution stored in the blood collection container main body is appropriately changed according to the size of the blood collection container main body, the amount of collected blood, and the like. The amount of the aqueous solution stored in the blood collection container main body is preferably 0.1 mL or more, more preferably 0.5 mL or more, and still more preferably 0.7 mL or more, meanwhile preferably 5 mL or less, more preferably 3 mL or less, and still more preferably 2.5 mL or less. When the amount of the aqueous solution is the above lower limit or more and the above upper limit or less, the effect of the present invention can be more effectively exhibited without excessively diluting the blood.

(Blood Collection Container Main Body)

The shape of the blood collection container main body is not particularly limited. The blood collection container main body is preferably a bottomed tubular container.

The material of the blood collection container main body is not particularly limited. Examples of the material of the blood collection container main body include thermoplastic resins such as polyethylene, polypropylene, polystyrene, polyethylene terephthalate, polymethyl methacrylate, and polyacrylonitrile; thermosetting resins such as unsaturated polyester resin, epoxy resin, or epoxy-acrylate resin; modified natural resins such as cellulose acetate, cellulose propionate, ethyl cellulose, and ethyl chitin; silicate glass soda such as lime glass, phosphosilicate glass, and borosilicate glass, and glass such as quartz glass. Only one kind of the material of the blood collection container main body may be used, or two or more kinds thereof may be used in combination.

(Plug)

The blood collection container preferably includes a plug. As the plug, a conventionally known plug can be used. The plug is preferably a plug made of a material or a shape that can be airtightly and liquid-tightly attached to an opening of the blood collection container main body. The plug is preferably configured such that a blood sampling needle can be inserted therethrough.

Examples of the plug include a plug having a shape fitted to the opening of the blood collection container main body and a sheet-shaped seal plug.

Further, the plug may be a plug including a plug main body such as a rubber plug and a cap member made of plastic or the like. In this case, it is possible to suppress a risk that the blood comes into contact with the human body when the plug is pulled out from the opening of the blood collection container main body after blood collection.

Examples of the material of the plug (or the plug main body) include synthetic resin, elastomer, rubber, and metal foil. Examples of the rubber include butyl rubber and halogenated butyl rubber. Examples of the metal foil include an aluminum foil. From a viewpoint of enhancing sealing performance, the material of the plug is preferably butyl rubber. The plug (or the plug main body) is preferably a butyl rubber plug.

(Other Details of Blood Collection Container)

The blood collection container is a blood collection container in which a predetermined amount of blood is collected. The predetermined amount of the blood is appropriately changed depending on the size, internal pressure, and the like of the blood collection container. The predetermined amount of the blood may be 1 mL or more, 2 mL or more, 4 mL or more, 12 mL or less, 11 ml or less, or 10 mL or less.

Physiological saline in an amount equivalent to the predetermined amount of the blood collected in the blood collection container is collected in the blood collection container to obtain a mixed liquid in which the physiological saline and the aqueous solution are mixed. For example, in a blood collection container in which 5 mL of blood is collected, 5 mL of physiological saline is collected in the blood collection container, and the physiological saline and the aqueous solution are mixed with inversion mixing or the like to obtain a mixed liquid. The osmotic pressure of the mixed liquid obtained by mixing the physiological saline and the aqueous solution is preferably 330 mOsm/L or more and 380 mOsm/L or less, or 440 mOsm/L or more. In this case, when blood is collected in the blood collection container, the specific gravity of white blood cells and red blood cells can be effectively increased, and contamination of plasma by white blood cells and red blood cells can be more effectively suppressed. Further, in this case, excessive stress on blood cells can be suppressed, and contamination by components in the blood cells can be more effectively suppressed.

When the osmotic pressure of the mixed liquid is 330 mOsm/L or more and 380 mOsm/L or less, the osmotic pressure of the mixed liquid is preferably 340 mOsm/L or more, and more preferably 350 mOsm/L or more, meanwhile preferably 375 mOsm/L or less, and more preferably 370 mOsm/L or less. When the osmotic pressure of the mixed liquid is the above lower limit or more and the above upper limit or less, the specific gravity of white blood cells and red blood cells can be effectively increased when blood is collected in the blood collection container, and contamination of plasma by white blood cells and red blood cells can be more effectively suppressed. Further, when the osmotic pressure of the mixed liquid is the above lower limit or more and the above upper limit or less, excessive stress on blood cells can be suppressed, and contamination by components in the blood cells can be more effectively suppressed.

When the osmotic pressure of the mixed liquid is 440 mOsm/L or more, the osmotic pressure of the mixed liquid is preferably 450 mOsm/L or more, and more preferably 500 mOsm/L or more, meanwhile preferably 1300 mOsm/L or less, and more preferably 1000 mOsm/L or less. When the osmotic pressure of the mixed liquid is the above lower limit or more and the above upper limit or less, the specific gravity of white blood cells and red blood cells can be effectively increased when blood is collected in the blood collection container, and contamination of plasma by white blood cells and red blood cells can be more effectively suppressed. Further, when the osmotic pressure of the mixed liquid is the above lower limit or more and the above upper limit or less, excessive stress on blood cells can be suppressed, and contamination by components in the blood cells can be more effectively suppressed.

The osmotic pressure of the mixed liquid is measured by a freezing point depression method using an osmometer (for example, "OM-6060" manufactured by ARKRAY, Inc.).

In the blood collection container, 3 mL or more, more preferably 4 mL or more, and preferably 11 mL or less, more preferably 7 mL or less of blood is collected relative to 1 mL of the stored aqueous solution. In this case, the effects of the present invention can be more effectively exhibited without excessively diluting the blood.

The blood collection container is preferably a blood collection tube. The blood collection container main body is preferably a blood collection tube main body.

The blood collection container is preferably used to separate plasma from blood. Further, the blood collection container is preferably used to separate cell free nucleic acids or extracellular vesicles in blood, and is preferably used to isolate cell free nucleic acids or extracellular vesicles in blood.

The blood collection container can be manufactured, for example, as follows.

The anticoagulant and the second solute are dissolved in water to obtain an aqueous solution. The obtained aqueous solution is added into the blood collection container main body. Before or after the aqueous solution is added, the plasma separation material is stored in the blood collection container main body.

FIG. 1 is a front cross-sectional view schematically illustrating a blood collection container according to one embodiment of the present invention.

A blood collection container 1 shown in FIG. 1 includes a blood collection container main body 2, a composition for plasma separation 3, an aqueous solution 4 containing an anticoagulant and a second solute, and a plug 5. The blood collection container main body 2 has an opening at one end and a bottom portion closed at the other end. The composition for plasma separation 3 is stored in the bottom portion of the blood collection container main body 2. The plug 5 is inserted into the opening of the blood collection container main body 2.

The aqueous solution 4 is disposed on a surface of the composition for plasma separation 3, more specifically, on an upper surface (a surface on one end side) of the composition for plasma separation 3. The aqueous solution 4 is disposed on the surface of the composition for plasma separation 3 when the blood collection container 1 is in an upright state. The anticoagulant and the second solute are stored in the blood collection container main body 2 in a state of being dissolved in water.

In the blood collection container according to the present invention, the composition for plasma separation may be disposed on a side wall surface of the blood collection container main body, and the aqueous solution may be disposed at the bottom portion of the blood collection container main body when the blood collection container is in an upright state. Further, the jig for plasma separation may be used instead of the composition for plasma separation.

The internal pressure of the blood collection container is not particularly limited. The blood collection container can also be used as a vacuum blood collection tube sealed by the plug after the inside is exhausted. In a case of the vacuum blood collection tube, it is possible to easily collect a certain amount of blood regardless of a technical difference of a blood-collecting operator.

From a viewpoint of preventing bacterial infection, the inside of the blood collection container is preferably sterilized in accordance with ISO or JIS standards.

(Method for Separating Plasma)

The blood collection container can be used to separate plasma from blood. The method for separating plasma according to the present invention includes a step of collecting blood into the blood collection container described above, and a step of centrifuging the blood collection container in which the blood has been collected.

The method for separating plasma according to the present invention preferably includes a step of mixing the collected blood with the aqueous solution between the step of collecting the blood and the step of centrifugation. Examples of the method for mixing the collected blood with the aqueous solution include inversion mixing.

Centrifugation conditions in the step of centrifugation are not particularly limited as long as the plasma and blood cells can be separated by forming a septal wall with the plasma separation material. Examples of the centrifugation conditions include a condition for centrifugation at 400 G or more and 4000 G or less for 10 minutes or more and 120 minutes or less.

(Method for Separating Cell Free Nucleic Acids and Method for Separating Extracellular Vesicles)

The method for separating cell free nucleic acids according to the present invention includes: a step of collecting blood into the blood collection container described above; a step of centrifuging the blood collection container in which the blood is collected to separate plasma from the blood; and a step of separating the cell free nucleic acids from the separated plasma.

The method for separating extracellular vesicles according to the present invention includes: a step of collecting blood into the blood collection container described above; a step of centrifuging the blood collection container in which the blood is collected to separate plasma from the blood; and a step of separating extracellular vesicles from the separated plasma.

The method for separating cell free nucleic acids and the method for separating extracellular vesicles according to the present invention preferably include a step of mixing the collected blood with the aqueous solution between the step of collecting the blood and the step of centrifugation. Examples of the method for mixing the collected blood with the aqueous solution include inversion mixing.

Centrifugation conditions in the step of centrifugation are not particularly limited as long as the plasma and blood cells can be separated by forming a septal wall with the plasma separation material. Examples of the centrifugation conditions include a condition for centrifugation at 400 G or more and 4000 G or less for 10 minutes or more and 120 minutes or less.

In the step of separating the cell free nucleic acids, the cell free nucleic acids can be separated from the plasma using a conventionally known method. Examples of the cell free nucleic acid include cell free DNA (cfDNA) and cell free RNA (cfRNA). Examples of the method for separating the cell free nucleic acids from the plasma include a method using a commercially available nucleic acid purification kit. By using a commercially available nucleic acid purification kit, cell free nucleic acids can be easily separated from plasma. Examples of commercially available products of the nucleic acid purification kit include QIAamp Circulating Nucleic Acid Kit (QIAGEN), QIAamp MinElute ccfDNA Kits (QIAGEN), and MagMAX Cell-Free DNA Isolation Kit (Applied biosystems).

In the step of separating the extracellular vesicles, the extracellular vesicles can be separated from the plasma using a conventionally known method.

Hereinafter, the present invention will be described in more detail with reference to examples. The present invention is not limited only to the following examples.

As a material of the composition for plasma separation, the following were prepared.

(Material of Organic Component Having Fluidity at 25° C.)

(Meth)Acrylic Resin:

Radical polymerization of 2-ethyl hexyl acrylate and butyl acrylate was performed in the presence of an azo-based polymerization initiator by a solution polymerization method to obtain a (meth)acrylic acid ester-based polymer having fluidity at 25° C.

Other Resins:

Petroleum resin ("REGALITE S5090" manufactured by Eastman Chemical Company)

Dicyclopentadiene resin 1 ("SUKOREZ SU500" manufactured by Kolon Industries Inc.)

Dicyclopentadiene resin 2 ("SUKOREZ SU90" manufactured by Kolon Industries Inc.)

Organic Compound:

Trimellitic acid ester (benzene polycarboxylic acid alkyl ester derivative, "MONOCIZER W700" manufactured by DIC Corporation)

(Inorganic Fine Powder)

Hydrophilic silica (fine powder silica, "200CF" manufactured by NIPPON AEROSIL CO., LTD.)

Hydrophobic silica (fine powder silica, "R974" manufactured by NIPPON AEROSIL CO., LTD.)

Titanium oxide powder (a second inorganic fine powder, "A-100" manufactured by ISHIHARA SANGYO KAISHA, LTD.)

(Other Components)

Silicone oil ("SF8410" manufactured by Dow Toray Co., Ltd.)

Organic gelling agent ("GEL ALL D" manufactured by New Japan Chemical Co., Ltd.)

1-Methyl-2-pyrrolidone (an auxiliary solvent)

Preparation of Compositions A and B for Plasma Separation:

Compositions A and B for plasma separation were prepared by mixing an organic component having fluidity at 25° C., an inorganic fine powder, and other components at a blending ratio shown in Table 1.

Preparation of Composition C for Plasma Separation:

Materials of an organic component having fluidity at 25° C. described in Table 1 were blended, heated and dissolved at 130° C., and mixed to prepare an organic component having fluidity at 25° ° C. Subsequently, an organic component having fluidity at 25° C., an inorganic fine powder, and other components were mixed at a blending ratio described in Table 1 to prepare a composition C for plasma separation.

TABLE 1

| | | | Composition A for plasma separation | Composition B for plasma separation | Composition C for plasma separation |
|---|---|---|---|---|---|
| Organic component having fluidity at 25° C. | (Meth)acrylic resin | wt % | 94.90 | 92.40 | — |
| | Petroleum resin | wt % | — | — | 14.50 |
| | Dicyclopentadiene resin 1 | wt % | — | — | 18.00 |
| | Dicyclopentadiene resin 2 | wt % | — | — | 19.70 |
| | Trimellitic acid ester | wt % | — | — | 44.90 |
| Inorganic fine powder | Fine powder silica Hydrophilic silica | wt % | 1.00 | 0.60 | 0.70 |
| | Fine powder silica Hydrophobic silica | wt % | 2.20 | 2.60 | 1.80 |
| | Titanium oxide powder | wt % | 1.80 | 4.30 | — |
| Other components | Silicone oil | wt % | 0.10 | 0.10 | — |
| | Organic gelling agent | wt % | — | — | 0.06 |
| | 1-Methyl-2-pyrrolidone | wt % | — | — | 0.34 |
| Total | | wt % | 100 | 100 | 100 |

One drop of the obtained composition for plasma separation was sequentially added dropwise to a saline solution at 25° C. in which the specific gravity was adjusted stepwise at an interval of 0.002, and the specific gravity was measured by floating and sinking in the saline solution. The specific gravity of the obtained composition for plasma separation at 25° C. is shown in Tables 2 to 4.

The following were prepared as a solute of the aqueous solution.

(Anticoagulant)

Dipotassium ethylenediaminetetraacetate dihydrate ($EDTA2K \cdot 2H_2O$)

(Second Solute)

Potassium Chloride (KCl)

Sodium Chloride (NaCl)

Sucrose

Glucose

Propylene glycol

Polyethylene glycol (PEG4000)

The following was prepared as a blood collection container main body.

A PET bottomed tube (a polyethylene terephthalate tube) having a length of 100 mm and an inner diameter of an opening portion of 14 mm Example 1

The anticoagulant and the second solute were dissolved in water to obtain an aqueous solution. The types and concentrations of blending components of the obtained aqueous solution are shown in Table 2.

The composition C for plasma separation (1.2 g) was stored in the bottom portion of the blood collection container main body. Further, 1 mL of the obtained aqueous solution was added onto the surface of the composition C for plasma separation. The inside of the blood collection container was decompressed so that a blood collection amount was 5 mL, and sealed with a butyl rubber plug. In this way, a blood collection container was prepared.

Examples 2 to 7 and Comparative Examples 2 to 4

The type of the composition for plasma separation and a composition of the aqueous solution were changed as shown in Tables 2 to 4. Further, in Example 5 and Comparative Examples 2 and 3, the inside of the blood collection container was decompressed so that the blood collection amount was 10 mL, and sealed with a butyl rubber plug. A blood collection container was prepared in the same manner as in Example 1 except for these.

Comparative Example 1

The anticoagulant of 32 parts by weight was dissolved in water of 68 parts by weight to obtain a mixed liquid. The composition C for plasma separation (1.2 g) was stored in the bottom portion of the blood collection container main body. Further, the obtained mixed liquid (60 mg) was applied to the inner wall surface of the blood collection container main body and dried. The inside of the blood collection container was decompressed so that the blood collection amount was 10 mL, and sealed with a butyl rubber plug. In this way, a blood collection container was prepared.

(Evaluation)

(1) Osmotic Pressure of Mixed Liquid physiological saline (5 mL) was collected in the blood collection container obtained in Examples 1 to 4, 6, and 7. Further, physiological saline (10 mL) was collected in the blood collection container obtained in Example 5. The physiological saline was collected and then mixed by inversion, and the physiological saline and the aqueous solution stored in the blood collection container were mixed to obtain a mixed liquid. The osmotic pressure of the obtained mixed liquid was measured by a freezing point depression method using an osmometer ("OM-6060" manufactured by ARKRAY, Inc.).

(2) Recovery Amount of cfDNA

The blood of three people was used, and the following operations were performed on each of them. Two blood collection containers obtained in each of Examples 1 to 4, 6, and 7 and Comparative Example 4 were prepared, and 5 mL of blood was collected, respectively. Further, two blood collection containers obtained in each of Example 5 and Comparative Examples 1 to 3 were prepared, and 10 mL of blood was collected, respectively. After the blood was collected, it was mixed by inversion, and the blood and the aqueous solution stored in the blood collection container were mixed. Next, the blood collection container was centrifuged at 1500 G for 15 minutes. After centrifugation, the plasma was located above the septal wall formed by the composition for plasma separation.

For one of the two blood collection containers after plasma separation, the plasma was collected from the blood collection container on the day when blood was collected. Further, for the remaining one of the two blood collection containers after the plasma separation, the blood collection container in a state where the plasma had been separated was stored at room temperature (25° C.) for 7 days, and then the plasma was collected from the blood collection container.

DNA contained in the collected plasma was purified using cfDNA purification kit ("QIAamp Circulating Nucleic Acid Kit" manufactured by QIAGEN). Note that, a purification operation of DNA was performed on the day when the plasma was collected from the blood collection container.

The concentration of DNA in an extraction liquid after purification was measured using Qubit dsDNA HS Assay kit (Invitrogen). Next, the concentration of cfDNA (the content of cfDNA contained per 1 mL of plasma) was calculated according to the following formula.

$$\text{cfDNA concentration (ng/plasma 1 mL)}=[A]\times[B]/[C]$$

[A]: Measurement of DNA concentration in extraction liquid after purification (ng/ml)

[B]: Total amount of extraction liquid after purification (mL)

[C]: Amount of plasma used for DNA purification (mL)

An average value of the concentration of cfDNA recovered from the plasma on the day of blood collection was defined as "cfDNA concentration (on the day of collection)", and the average value of the concentration of cfDNA recovered from the plasma after storage for 7 days was defined as "cfDNA concentration (storage for 7 days)". Further, the difference between the cfDNA concentration (storage for 7 days) and the cfDNA concentration (on the day of collection) was defined as an "increase amount of the cfDNA concentration". Note that, the average value of the concentration of cfDNA is an average value of results obtained using the blood of three people.

The recovery amount of cfDNA was determined according to the following criteria. Note that, the larger the amount of white blood cells by which the plasma is contaminated and the more unstable the white blood cells in the plasma, the larger the increase amount in the cfDNA concentration accompanying the destruction of the white blood cells during storage. Therefore, as the increase amount of the cfDNA concentration is smaller, contamination of the plasma by white blood cells and contamination of the plasma by components in white blood cells are suppressed.

<Criteria for Determining Recovery Amount of cfDNA> oo: The increase amount in cfDNA concentration is less than 20 ng/plasma 1 mL o: The increase amount of cfDNA concentration is 20 ng/plasma 1 mL or more and less than 100 ng/plasma 1 mL x: The increase amount of cfDNA concentration is 100 ng/plasma 1 mL or more.

The configuration and results are shown in Tables 2 to 4 below. Note that, in the table, the concentration of the anticoagulant means the concentration of EDTA2K instead of the concentration of EDTA2K·$2H_2O$.

TABLE 2

| | | | | Example 1 | Example 2 | Example 3 | Example 4 |
|---|---|---|---|---|---|---|---|
| Aqueous solution | Anticoagulant | EDTA2K•$2H_2O$ | mM | 20 | 20 | 150 | 20 |
| | Second solute | KCl | mM | | 350 | | 1200 |
| | | NaCl | mM | 370 | | 430 | |
| | | Sucrose | mM | | | 1100 | |
| | | Glucose | mM | | | | |
| | | Propylene glycol | MM | | | | |
| | | PEG4000 | mM | | | | |
| | Total concentration of solute | | mM | 390 | 370 | 1680 | 1220 |
| Amount of aqueous solution stored in blood collection container | | | mL | 1 | 1 | 1 | 1 |
| Composition for plasma separation | | Type | — | C | C | C | A |
| | | Specific gravity at 25° C. | — | 1.045 | 1.045 | 1.045 | 1.065 |
| Amount of collected blood | | | mL | 5 | 5 | 5 | 5 |
| Evaluation | Osmotic pressure of mixed liquid | | mOsm/L | 365 | 354 | 675 | 628 |
| | Recovery amount of cfDNA | cfDNA concentration (on the day of collection) | ng/plasma 1 mL | 15 | 16 | 14 | 15 |
| | | cfDNA concentration (storage for 7 days) | ng/plasma 1 mL | 77 | 74 | 16 | 18 |
| | | Increase amount in cfDNA concentration | ng/plasma 1 mL | 62 | 58 | 2 | 3 |
| | | | Determination | o | o | oo | oo |

TABLE 3

| | | | | Example 5 | Example 6 | Example 7 |
|---|---|---|---|---|---|---|
| Aqueous solution | Anticoagulant | $EDTA2K{\bullet}2H_2O$ | mM | 20 | 20 | 20 |
| | Second solute | KCl | mM | 1200 | | |
| | | NaCl | mM | | 430 | 220 |
| | | Sucrose | mM | | | |
| | | Glucose | mM | | 1100 | |
| | | Propylene glycol | mM | | 4000 | |
| | | PEG4000 | mM | | | 30 |
| | Total concentration of solute | | mM | 1220 | 5550 | 270 |
| Amount of aqueous solution stored in blood collection container | | | mL | 1 | 1 | 1 |
| Composition for plasma separation | | Type | — | C | B | C |
| | | Specific gravity at 25° C. | — | 1.045 | 1.085 | 1.045 |
| Amount of collected blood | | | | 10 | 5 | 5 |
| Evaluation | Osmotic pressure of mixed liquid | | mOsm/L | 472 | 1241 | 332 |
| | Recovery amount of cfDNA | cfDNA concentration (on the day of collection) | ng/plasma 1 mL | 15 | 14 | 18 |
| | | cfDNA concentration (storage for 7 days) | ng/plasma 1 mL | 72 | 17 | 85 |
| | | Increase amount in cfDNA concentration | ng/plasma 1 mL | 57 | 3 | 67 |
| | | | Determination | ○ | ○○ | ○ |

TABLE 4

| | | | | Comparative Example 1 | Comparative Example 2 | Comparative Example 3 | Comparative Example 4 |
|---|---|---|---|---|---|---|---|
| Aqueous solution | Anticoagulant | $EDTA2K{\bullet}2H_2O$ | mM | | 100 | 120 | 100 |
| | Second solute | KCl | mM | | | | |
| | | NaCl | mM | | 500 | 500 | 100 |
| | | Sucrose | mM | | | | |
| | | Glucose | mM | | 350 | | 700 |
| | | Propylene glycol | mM | | | | |
| | | PEG4000 | mM | | | | |
| | Total concentration of solute | | mM | | 950 | 620 | 900 |
| Amount of aqueous solution contained in blood collection container | | | mL | | 1 | 1 | 1 |
| Composition for plasma separation | | Type | — | C | C | C | C |
| | | Specific gravity at 25° C. | — | 1.045 | 1.045 | 1.045 | 1.045 |
| Amount of collected blood | | | mL | 10 | 10 | 10 | 5 |
| Evaluation | Osmotic pressure of mixed liquid | | mOsm/L | — | — | — | — |
| | Recovery amount of cfDNA | cfDNA concentration (on the day of collection) | ng/plasma 1 mL | 12 | 17 | 15 | 14 |
| | | cfDNA concentration (storage for 7 days) | ng/plasma 1 mL | 634 | 240 | 131 | 187 |
| | | Increase amount in cfDNA concentration | ng/plasma 1 mL | 622 | 223 | 116 | 173 |
| | | | Determination | x | x | x | x |

EXPLANATION OF SYMBOLS

1: Blood collection container
2: Blood collection container main body
3: Composition for plasma separation
4: Aqueous solution
5: Plug

The invention claimed is:

1. A blood collection container comprising:

a blood collection container main body;

a plasma separation material stored in the blood collection container main body; and an aqueous solution stored in the blood collection container main body, a solute contained in the aqueous solution containing an anticoagulant and a second solute other than an anticoagulant, the second solute including an inorganic salt, the concentration of the anticoagulant in the aqueous solution being 50 mM or less, the solute in the aqueous solution having a total concentration of 250 mM or more and 450 mM or less, or 1200 mM or more, when the total concentration of the solute in the aqueous solution is 250 mM or more and 450 mM or less, the concentration of the inorganic salt in the aqueous solution is 200 mM or more.

2. The blood collection container according to claim 1, wherein the total concentration of the solute in the aqueous solution is 250 mM or more and 390 mM or less, or 1200 mM or more and 6500 mM or less.

3. The blood collection container according to claim 1, wherein the second solute includes a saccharide.

4. The blood collection container according to claim 1, wherein the inorganic salt includes a sodium salt or a potassium salt.

5. A method for separating cell free nucleic acids, the method comprising:

a step of collecting blood in the blood collection container according to claim 4;

a step of centrifuging the blood collection container in which the blood has been collected to separate plasma from the blood; and a step of separating cell free nucleic acids from the separated plasma.

6. A method for separating extracellular vesicles, the method comprising:

a step of collecting blood in the blood collection container according to claim 4;

a step of centrifuging the blood collection container in which the blood has been collected to separate plasma from the blood; and a step of separating extracellular vesicles from the separated plasma.

7. The blood collection container according to claim 1, wherein the second solute includes a saccharide, and the saccharide includes glucose, sucrose, or trehalose.

8. A method for separating cell free nucleic acids, the method comprising:

a step of collecting blood in the blood collection container according to claim 7;

a step of centrifuging the blood collection container in which the blood has been collected to separate plasma from the blood; and a step of separating cell free nucleic acids from the separated plasma.

9. A method for separating extracellular vesicles, the method comprising:

a step of collecting blood in the blood collection container according to claim 7;

a step of centrifuging the blood collection container in which the blood has been collected to separate plasma from the blood; and a step of separating extracellular vesicles from the separated plasma.

10. The blood collection container according to claim 1, wherein the anticoagulant is EDTA, a metal salt of EDTA, heparin, a metal salt of heparin, or sodium citrate.

11. The blood collection container according to claim 1, being a blood collection container in which a predetermined amount of blood is collected, wherein when physiological saline in an amount equivalent to a predetermined amount of blood collected in the blood collection container is collected in the blood collection container to obtain a mixed liquid in which the physiological saline and the aqueous solution are mixed, an osmotic pressure of the mixed liquid is 330 mOsm/L or more and 380 mOsm/L or less, or 440 mOsm/L or more and 1300 mOsm/L or less.

12. The blood collection container according to claim 1, wherein a specific gravity of the plasma separation material at 25° C. is 1.030 or more and 1.120 or less.

13. The blood collection container according to claim 1, wherein the plasma separation material is a composition for plasma separation, the composition for plasma separation containing an organic component having fluidity at 25° C. and an inorganic fine powder.

14. The blood collection container according to claim 13, wherein the organic component includes a resin, and the inorganic fine powder includes fine powder silica.

15. The blood collection container according to claim 14, wherein the fine powder silica includes hydrophilic silica.

16. The blood collection container according to claim 15, wherein a content of the hydrophilic silica is 0.01 wt % or more and 2.50 wt % or less in 100 wt % of the composition for plasma separation.

17. The blood collection container of claim 14, wherein the fine powder silica includes hydrophilic silica and hydrophobic silica.

18. The blood collection container according to claim 14, wherein a specific gravity of the composition for plasma separation at 25° C. is 1.050 or more, and the inorganic fine powder contains a second inorganic fine powder having a specific gravity larger than a specific gravity of the fine powder silica.

19. The blood collection container according to claim 14, wherein the resin includes a petroleum resin, a cyclopentadiene-based resin, a polyester resin, or a (meth)acrylic resin.

20. The blood collection container according to claim 1, wherein the blood collection container is configured to separate cell free nucleic acids or extracellular vesicles in blood.

21. A method for separating plasma, the method comprising:

a step of collecting blood in the blood collection container according to claim 1, and a step of centrifuging the blood collection container in which the blood has been collected.

22. A method for separating cell free nucleic acids, the method comprising:

a step of collecting blood in the blood collection container according to claim 1;

a step of centrifuging the blood collection container in which the blood has been collected to separate plasma from the blood; and a step of separating cell free nucleic acids from the separated plasma.

23. A method for separating extracellular vesicles, the method comprising:

a step of collecting blood in the blood collection container according to claim 1;

a step of centrifuging the blood collection container in which the blood has been collected to separate plasma from the blood; and a step of separating extracellular vesicles from the separated plasma.

* * * * *